(12) United States Patent
Meskens et al.

(10) Patent No.: US 10,265,533 B2
(45) Date of Patent: Apr. 23, 2019

(54) IMPLANT HEAT PROTECTION

(71) Applicant: Cochlear Limited, Macquarie University, NSW (AU)

(72) Inventors: Werner Meskens, Mechelen (BE); Oliver John Ridler, Macquarie University (AU); Robert Graham Bennett, Macquarie University (AU)

(73) Assignee: COCHLEAR LIMITED, Macquarie University (AU)

( * ) Notice: Subject to any disclaimer, the term of this patent is extended or adjusted under 35 U.S.C. 154(b) by 80 days.

(21) Appl. No.: 15/465,676

(22) Filed: Mar. 22, 2017

(65) Prior Publication Data

US 2018/0272130 A1    Sep. 27, 2018

(51) Int. Cl.
| A61N 1/00 | (2006.01) |
| A61N 1/378 | (2006.01) |
| A61N 1/372 | (2006.01) |
| A61N 1/36 | (2006.01) |

(52) U.S. Cl.
CPC ....... *A61N 1/3787* (2013.01); *A61N 1/36036* (2017.08); *A61N 1/37252* (2013.01)

(58) Field of Classification Search
CPC .............. A61N 1/36032; A61N 1/3787; A61N 1/36036; A61N 1/37252
See application file for complete search history.

(56) References Cited

U.S. PATENT DOCUMENTS

| 7,209,792 | B1 | 4/2007 | Parramon et al. |
| 2005/0288739 | A1* | 12/2005 | Hassler, Jr. .......... A61N 1/3787 607/61 |
| 2007/0109708 | A1* | 5/2007 | Hussman .................. H02J 1/00 361/113 |
| 2011/0046699 | A1 | 2/2011 | Mazanec |
| 2011/0121777 | A1* | 5/2011 | Carbunaru ........... A61N 1/3787 320/108 |
| 2014/0025137 | A1* | 1/2014 | Meskens .............. A61N 1/3787 607/57 |
| 2014/0266022 | A1 | 9/2014 | Degen et al. |

* cited by examiner

*Primary Examiner* — George Manuel
(74) *Attorney, Agent, or Firm* — Edell, Shapiro & Finnan, LLC

(57) ABSTRACT

Presented herein are techniques for protecting an implantable component of a medical device from the buildup of excessive heat following a charging process. In one embodiment, the implantable component includes a resonant tank circuit that includes an implantable coil that receives power from the external charging device via an inductive link. The implantable component includes a rechargeable battery that is electrically connected to the resonant tank circuit and that can be recharged using the power received from the external charging device. A controller in the implantable component is configured to determine when charging of the rechargeable battery should be terminated and, in response, detune the resonant tank circuit in accordance with a predetermined pattern to signal to the external charging device that charging of the rechargeable battery should be terminated.

24 Claims, 8 Drawing Sheets

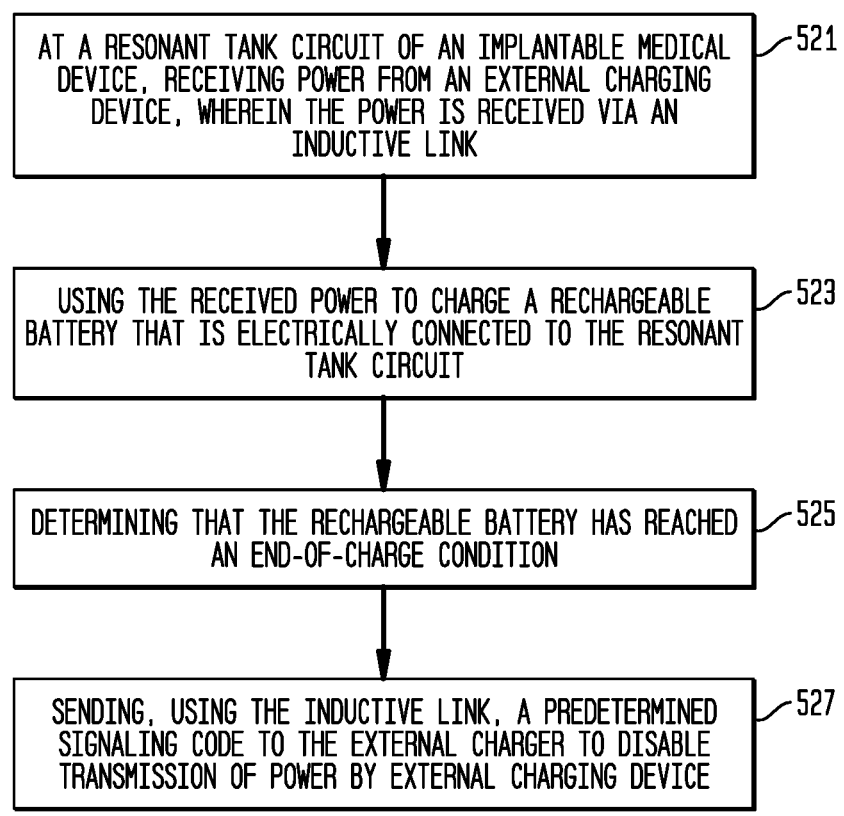

US 10,265,533 B2

IMPLANT HEAT PROTECTION

BACKGROUND

Field of the Invention

The present invention relates generally to implantable medical devices.

Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify the anatomy or a physiological process. Many of these functional components utilize power and/or data received from external components that are part of, or operate in conjunction with, the implantable medical device.

SUMMARY

In one aspect an implantable medical device is provided. The implantable medical device comprises: a resonant tank circuit including an implantable coil coupled to an external coil of an external charging device via an inductive link so as to receive power from the external charging device via the inductive link; a rechargeable battery electrically connected to the resonant tank circuit so as to be charged using the power received from the external charging device; and a controller configured to: determine when charging of the rechargeable battery should be terminated, detune the resonant tank circuit in accordance with a predetermined pattern to signal to the external charging device that charging of the rechargeable battery should be terminated, and electrically disconnect the rechargeable battery from the resonant tank circuit.

In another aspect a method is provided. The method comprises: at a resonant tank circuit of an implantable medical device tuned to a first resonant frequency, receiving power from an external charging device via an inductive power link; using the received power to charge a rechargeable battery that is electrically connected to the resonant tank circuit tuned; determining that the rechargeable battery has reached an end-of-charge condition; sending, using the inductive power link, a predetermined signaling code to the external charger to disable transmission of power by external charging device; and after sending the predetermined signaling code, detuning the resonant tank circuit to a second frequency.

In another aspect a method is provided. The method comprises: transferring power signals from an external coil of a charging device to an implantable coil of an implantable medical device, wherein the external coil and implantable coil are coupled via an inductive link; monitoring the inductive link for a predetermined implant detuning sequence; and upon detection of the predetermined implant detuning sequence, terminating transfer of the power signals from the external coil to the implantable coil.

In another aspect an implantable medical device is provided. The implantable medical device comprises: a resonant tank circuit including an implantable coil coupled to an external coil of an external charging device via an inductive link so as to receive power from the external charging device via the inductive link; a rechargeable battery electrically connected to the resonant tank circuit so as to be charged using the power received from the external charging device over a first frequency; and a controller configured to: determine when charging of the rechargeable battery should be terminated, change the arrangement of the resonant tank circuit in accordance with a predetermined sequence so as to cause a corresponding sequence of detectable load changes at the external charging device; and detune the resonant tank circuit to a second frequency.

BRIEF DESCRIPTION OF THE DRAWINGS

Embodiments of the present invention are described herein in conjunction with the accompanying drawings, in which:

FIG. 5 is a high-level flowchart illustrating a method, in accordance with embodiments presented herein.

DETAILED DESCRIPTION

Embodiments presented herein are generally directed to techniques for protecting an implantable component of a medical device from the buildup of excessive heat following a charging process. In particular, the implantable component comprises a resonant tank circuit that includes an implantable coil that receives power from the external charging device via an inductive link. The implantable component also includes a rechargeable battery that is electrically connected to the resonant tank circuit and that can be recharged using the power received from the external charging device. A controller in the implantable component is configured to determine when charging of the rechargeable battery should be terminated and, in response, change the arrangement of the resonant tank circuit in accordance with a predetermined sequence/pattern so as to cause a corresponding sequence/pattern of detectable load changes at the external device. The predetermined sequence of load changes, which is referred to herein as an "implant detuning sequence" or "implant detuning" of the inductive link, is detectable at the external charging device and signals to the external charging device that charging of the rechargeable battery should be terminated. The controller can also electrically disconnect the rechargeable battery from the resonant tank circuit and alter the implant resonant circuit characteristics.

There are a number of different types of implantable medical device systems in which embodiments of the present invention may be implemented. However, merely for ease of illustration, the techniques presented herein are primarily described with reference to one type of implantable medical device system, namely a cochlear implant system. It is to be appreciated that the techniques presented herein may be used in other auditory prosthesis systems, such as systems that include auditory brainstem stimulators, electro-acoustic hearing prostheses, bimodal hearing prostheses, etc. and/or any other partially or fully implantable medical device system now known or later developed, including implantable pacemakers, defibrillators, deep brain stimulators, functional electrical stimulation devices, etc.

Figure 1:
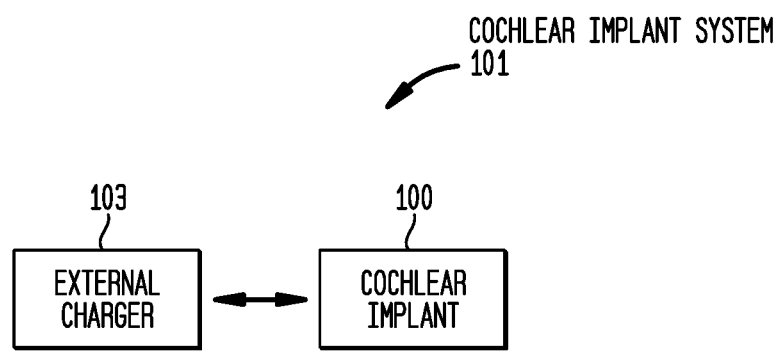
FIG. 1 is a block diagram illustrating a cochlear implant system, in accordance with embodiments presented herein.

FIG. 1 is block diagram of an exemplary cochlear implant system 101 in which embodiments presented herein are implemented. The cochlear implant system 101 comprises a cochlear implant 100 and an external charging device, sometimes referred to herein as an inductive or external charger 103. The external charger 103 may have a number of different forms, such as a headpiece coil wired to a battery pack, a headpiece power charger in the shape of a button, etc.

As described below, the cochlear implant 100 comprises a rechargeable battery (not shown in FIG. 1) that is configured to be recharged using power signals received from the external charger 103 over/via an inductive power link. Also as described below, the cochlear implant 100 includes a resonant tank circuit (not shown in FIG. 1) and an implant controller (also not shown in FIG. 1) that controls one or more characteristics of the resonant tank circuit residing in the cochlear implant 100 (e.g., the arrangement/configuration of the resonant tank circuit) so as to detune the resonant tank circuit and terminate the transmission of power signals from the external charger 103.

Figure 2:
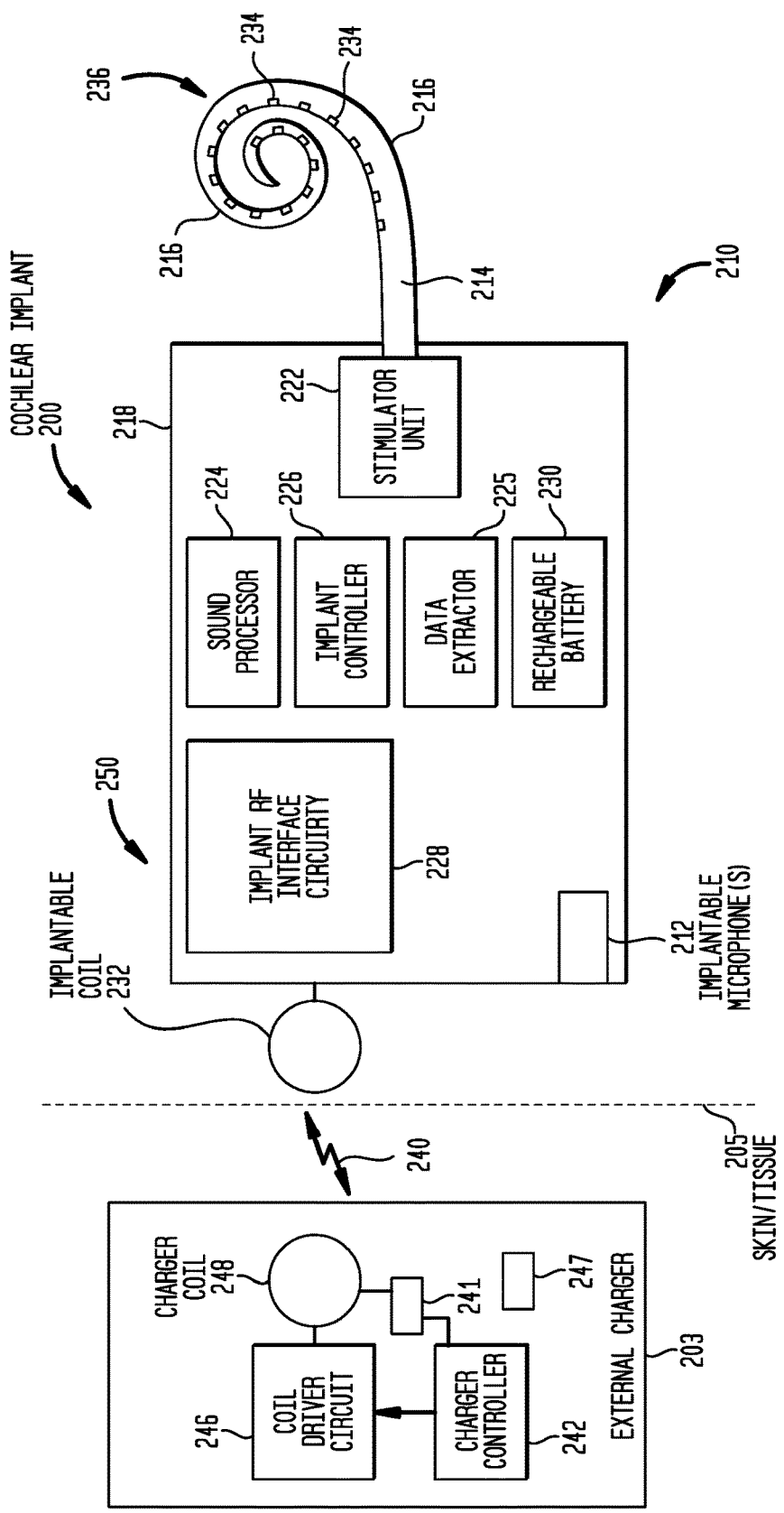
FIG. 2 is a block diagram of a cochlear implant, in accordance with embodiments presented herein.

It is to be appreciated that the cochlear implant 100 of FIG. 1, as well as the external charger 103 of FIG. 1, may each have a number of different arrangements. FIG. 2 is a block diagram illustrating one example arrangement for the cochlear implant 100, referred to as cochlear implant 200, as well as one example arrangement for external charger 103, referred to as external charger 203.

The cochlear implant 200 is a totally implantable cochlear implant where all components of the cochlear implant are configured to be implanted under the skin/tissue 205 of a recipient. Because all components are implantable, cochlear implant 200 operates, for at least a finite period of time, without the presence of an external device (e.g., without external charger 203).

Cochlear implant 200 includes an implant body (main module) 210, a lead region 214, and an elongate intra-cochlear stimulating assembly 216. The implant body 210 generally comprises a hermetically-sealed housing 218 in which a stimulator unit (stimulation electronics) 222, a sound processor 224, a data extractor component or data processor 225, an implant controller 226 (i.e., battery and power management component or battery processor), implant radio frequency (RF) interface circuitry 228, one or more implantable microphones 212, and a rechargeable battery 230 are disposed.

The implant body 210 also includes an internal/implantable coil 232 that is located external to the housing 218 and a resonant tank circuit 250 that, as described further below, is formed by the implantable coil 232 and one or more elements of the implant RF interface circuitry 228. The implantable coil 232 is connected to the implant RF interface circuitry 228 within the housing 218 via a hermetic feedthrough (not shown in FIG. 2). Implantable coil 232 is typically a wire antenna coil comprised of multiple turns of electrically insulated single-strand or multi-strand platinum or gold wire. The electrical insulation of implantable coil 232 is provided by a flexible molding (e.g., silicone molding), which is not shown in FIG. 2. Generally, a permanent magnet is fixed relative to the implantable coil 232 for magnetic coupling with another magnet in an external device.

Elongate stimulating assembly 216 is configured to be at least partially implanted in the recipient's cochlea (not shown) and includes a plurality of longitudinally spaced intra-cochlear electrical stimulating contacts (electrodes) 234 that collectively form a contact array 236 for delivery of electrical stimulation (current) to the recipient's cochlea. Stimulating assembly 216 extends through an opening in the cochlea (e.g., cochleostomy, the round window, etc.) and has a proximal end connected to the stimulator unit 222 via the lead region 214 and a hermetic feedthrough (not shown in FIG. 2). Lead region 214 includes one or more conductors (wires) that electrically couple the electrodes 234 to the stimulator unit 222. In this way, cochlear implant 200 electrically stimulates the recipient's auditory nerve cells, bypassing absent or defective hair cells that normally transduce acoustic vibrations into neural activity, in a manner that causes the recipient to perceive one or more components of the received sound signals.

The one or more implantable microphones 212 are configured to detect/receive input sound signals that are provided to the sound processor 224. The sound processor 212 is configured to execute sound processing and coding to convert the received sound signals into output signals for use by the stimulator unit 222 in delivering electrical stimulation (current) to the recipient via electrodes 234.

The a resonant tank circuit 250 is used by the cochlear implant 200 to receive power/current signals from an external charger (e.g., external charger 103, 203) via an RF link, sometimes referred to herein as an inductive power link, which is represented in FIG. 2 by arrow 240. The external charger 203 comprises a charger controller 242, a coil driver 246, and one or more charger or external coils 248 and a sensor 241. In one embodiment, the sensor 241 is an implant impedance sensor configured to sense the current going through the coil in the external charger device 203. In alternative embodiments, the sensor 241 is another type of sensor configured to measure the back scattering or reflected load changes from the coupled cochlear implant 200. The external charger 203 is configured to send power to the cochlear implant 200 via the inductive power link 240 formed between charger coil 248 and the implantable coil 232. More specifically, when the implantable coil 232 is "docked" with external charger 203 (e.g., when the implantable coil 232 and the charger coil 248 are located proximate to one another and aligned to form an inductive coupling), charger controller 242 uses coil driver circuit 246 and charger coil 248 to create a magnetic field. In one example, the charger coil 248 generates a 6.78 Megahertz (MHz) magnetic field that induces current flow in the implantable coil 232. The implantable coil 232 is part of the resonant tank circuit 250, which can use the current inducted in the implantable coil 232 to charge the rechargeable battery 230.

The rechargeable battery 230 is configured to store the energy needed to power the other elements of the cochlear implant 200, as well as to provide the current needed to electrically stimulate the recipient's cochlea. The resonant tank circuit 250 is configured to operate under the control of the implant controller 226 so as to charge the rechargeable battery 230 using the power received from the external charger 203.

More specifically, the resonant tank circuit 250 includes an adjustable resonant configuration that enables the selection of at least two different resonant/tuning frequencies (i.e., a frequency shift option), where only one of the resonant frequencies is used to receive power from the external charger 203. For ease of illustration, embodiments presented herein will be primarily described herein with reference to a resonant tank circuit that can be switched between a resonant frequency of approximately 5 MHz and a resonant frequency of approximately 6.78 MHz. However, it is to be appreciated that these two specific resonant frequencies are illustrative and that the techniques presented herein may be used with other circuitry having different tuning frequencies.

In the illustrative examples that can be switched between 5 MHz and 6.78 MHz, the 5 MHz resonant frequency supports a combined power data transfer (e.g., On-off-keying (OOK)) or a separated power and data transfer (Time division multiple access (TDMA)) between cochlear implant 200 and an external device. The 6.78 MHz resonant frequency is utilized only for the purpose of transferring power from external charger 203 (or another external charging device) to the rechargeable battery 230 during recharge operations (i.e., the 6.78 MHz frequency is used for charging the battery 230).

The total amount of energy a rechargeable battery can store at any one time, often measured in terms of milliamp Hours (mAhs), is referred to herein as the maximum "capacity" of the battery. Rechargeable batteries, such as rechargeable battery 230, can only be charged to their associated maximum capacity using power received from the external charger 203. Continuing to charge a rechargeable battery after the battery is fully charged can reduce the longevity of the battery itself and/or generate heat in the circuitry associated with the battery. Therefore the charger controller 242 of the external charger may decide to cease the charging operation and/or the implant battery may be electrically disconnected from the implant coil through a switch controlled by the implant controller 226.

Implantable components typically include overvoltage protections, such as Zener diodes, Tranzorbs, etc. that are designed to protect the implant from overvoltage by dissipating part of the received RF energy as heat once the implant battery is disconnected. However, environments with large magnetic (H) or electromagnetic (EM) fields emanating from industrial, scientific and medical (ISM) equipment (i.e. operating at 6.78 MHz) still have the potential to cause excessive heating that damages or causes failure of these overvoltage protections.

As such, presented herein are techniques for protecting cochlear implant 200 from the buildup of excessive heat following the charging of rechargeable battery 230 or by the presence of large H or EM fields from ISM equipment. More specifically, in accordance with embodiments presented herein, once charging of the rechargeable battery 230 should be terminated (e.g., the battery is fully charged), cochlear implant 200 is configured to initiate several operations to protect the rechargeable battery 230, as well as circuitry associated with the battery and the implant, from excessive heat buildup. First, when the implant controller 226 determines that the rechargeable battery 230 has reached an end-of-charge condition (e.g., is fully charged), the implant controller 226 is configured to detune the implant resonant tank of the inductive power link 240 in accordance with a predetermined pattern so as to signal to the external charger 203 that charging of the rechargeable battery 230 should be terminated. Second, after signaling to the external charger 203 that charging of the rechargeable battery 230 should be terminated, the implant controller 226 electrically disconnects the rechargeable battery 230 from the resonant tank circuit 250. Third, the implant controller 226 is configured to adjust one or more characteristics of the resonant tank circuit 250 (e.g., the configuration of the resonant tank circuit) so as to shift the tuning frequency of the resonant tank circuit from 6.78 MHz (optimal for charging) to 5 MHz. This is done at the end of the charging cycle in order to reduce the heat dissipation in the implant (blind power) from 6.78 MHz fields.

In general, the above operations protect the implant from excessive heat buildup that could result from continued delivery of energy from the external charger 203. For example, electrical disconnection of the rechargeable battery 230 from the resonant tank circuit 250 prevents the transfer of further energy to the battery itself (i.e., the battery no longer receives the energy transferred from the external charger 203). However, disconnection of the rechargeable battery 230 may cause the energy received from the external charger 203 to be absorbed by implant circuit protections (e.g., Zener diode components limiting the positive and the negative RF cycle, Tranzorb components placed in parallel with the battery, etc.) in the resonant tank circuit 250, thereby causing excessive overvoltage and heat buildup. That is, power that cannot be provided to the rechargeable battery 230 (i.e., due to the disconnection thereof) can cause damage the resonant tank circuit 250. Therefore, before the rechargeable battery 230 is disconnected, the implant detuning signaling/sequence is used to proactively disable the external charger 203 (i.e., cause the external charger to stop transmitting power) and, accordingly, to prevent damage to the circuit protections. The tuning frequency shift from 6.78 MHz to 5 MHz is a safety mechanism so minimize power transfer, should the external charger 203 continue to transfer power even after detecting the implant detuning (implant detuning sequence) via the inductive power link 240.

Figure 3A:
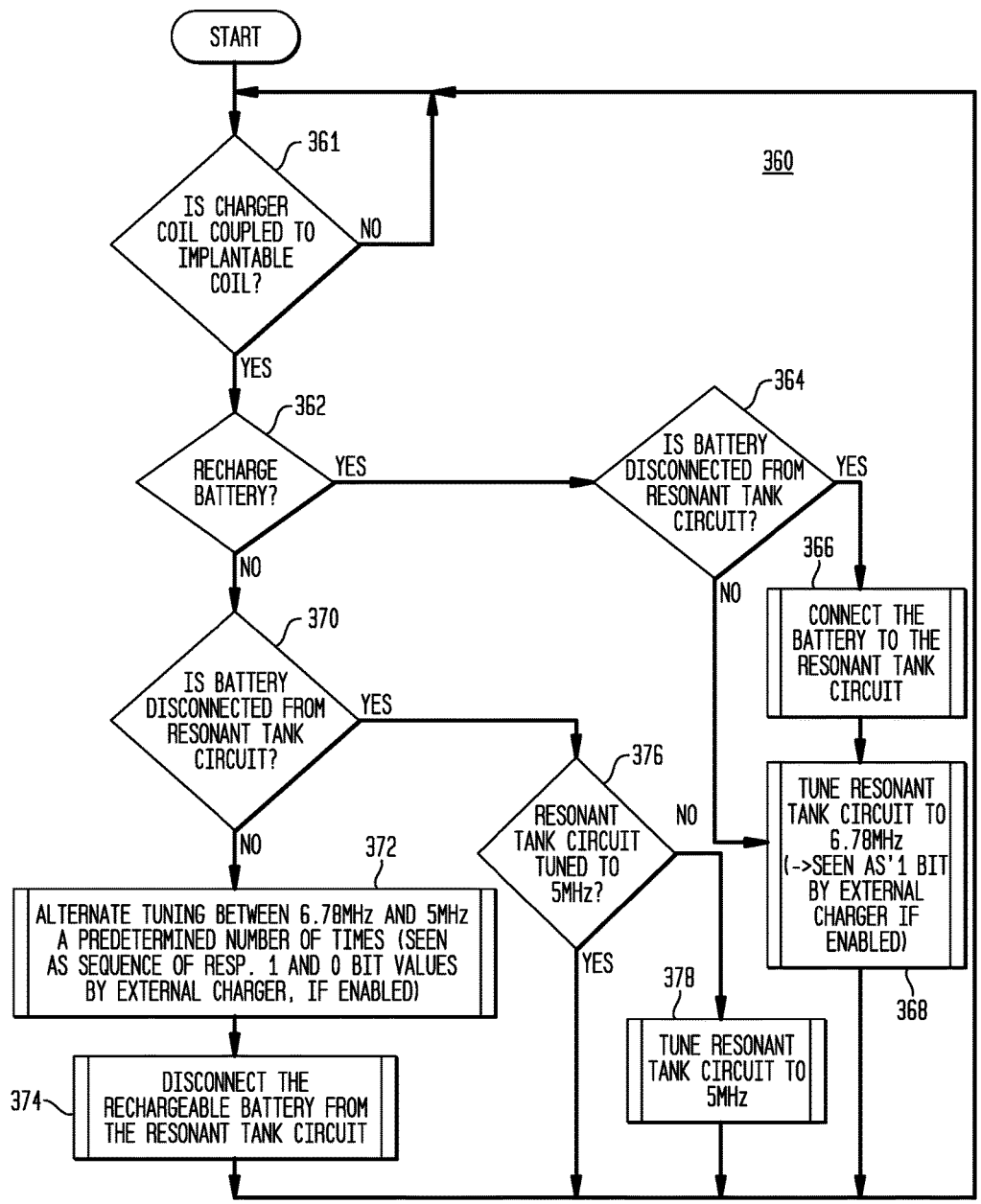
FIG. 3A is a flowchart illustrating operations of a cochlear implant, in accordance with embodiments presented herein.
Figure 3B:
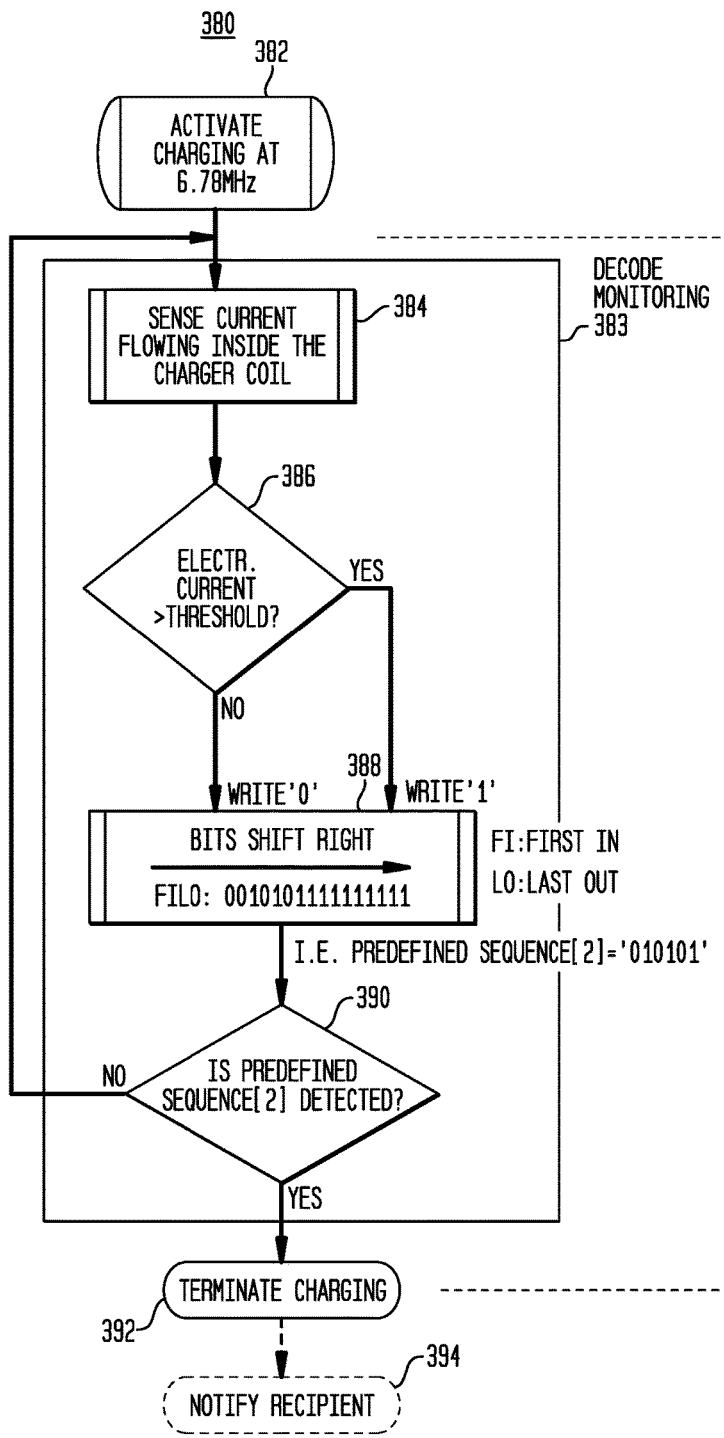
FIG. 3B is a flowchart illustrating operations of an external charger, in accordance with embodiments presented herein.

FIG. 3A is a flowchart illustrating operations of an implantable component in accordance with embodiments presented herein in order to protect the implantable component from heat upon completion of battery charging by an external charger. FIG. 3B is a flowchart illustrating corresponding operations of the external charger based on the operations of the implant in FIG. 3A. For ease of illustration, the flowcharts of FIGS. 3A and 3B are described with reference to the arrangement shown in FIG. 2.

The method 360 of FIG. 3A begins at 361 where the cochlear implant 200 monitors for the presence of the charger coil 248 (i.e., continually, periodically, etc. determines whether or not the charger coil 248 of the external charger 203 is coupled to the implantable coil 232). Once it is determined that the charger coil 248 of the external charger 203 is coupled to the implantable coil 232, method 360 proceeds to 362 where a determination is made as to whether or not the rechargeable battery 230 should be charged. This determination may be made, for example, by the implant controller 226. If it is determined that the rechargeable battery 230 should be charged, then a determination is made at 364 as to whether or not the rechargeable battery 230 is disconnected from the resonant tank circuit 250.

If the rechargeable battery 230 is not disconnected from the resonant tank circuit 250 (i.e., is connected to the circuit) then method 360 proceeds to 368. However, if the rechargeable battery 230 is disconnected from the resonant tank circuit 250, then the rechargeable battery 230 is connected to the resonant tank circuit 250 at 366. The method 360 then proceeds to 368.

At 368, the resonant tank circuit 250 is tuned to 6.78 MHz. Therefore, after 368, the cochlear implant 200 is optimally arranged to receive power from external charger 203. The operations of 362, 364, 366, and 368 are repeated (each as dictated above) until a determination is made at 362 that the rechargeable battery 230 should no longer be charged (e.g., charging should be terminated).

Once it is determined at 362 that the rechargeable battery 230 should no longer be charged, then method 360 proceeds to 370 where a determination is made as to whether the rechargeable battery 230 is disconnected from the resonant tank circuit 250. If the rechargeable battery 230 is not disconnected from the resonant tank circuit 250, then at 372 the implant controller 226 is configured to alter/adjust one or more characteristics of the resonant tank circuit 250 in order to detune the implant resonant tank (forming part of the inductive power link 240) in accordance with a predetermined pattern/sequence. The predetermined implant detuning sequence signals to the external charger 203 that the rechargeable battery 230 has reached an end-of-charge condition (i.e., should no longer be charged). In other words, the implant detuning sequence is used to inform the external charger 203 that the external charger 203 should terminate/disable the transmission of power to the cochlear implant 200.

The implant detuning of the resonant tank circuit 250 is caused by different arrangements of the resonant tank circuit 250 (set by the implant controller 226) that, in turn, cause variations in the current flowing through charger coil 248 in the external charger 203. That is, the charger coil 248 and the implantable coil 232 are closely coupled to one another and the charger coil 248 transmits a continuous time-varying RF carrier signal (i.e., wave). As such, changes in the resonant tank circuit 250 that affect the impedance of the resonant tank circuit will, due to the coupling between the charger coil 248 and the implantable coil 232, cause an impedance change (referred sometimes as reflected load) at the charger coil 248 (e.g., change of the load at the charger coil 248 sensed by the implant impedance sensor 241). This impedance/load change sensed at the charger coil 248, in turn, affects the amount of current flowing through the charger coil 248. As described further below, changing the arrangement of the resonant tank circuit 250 in accordance with a predetermined sequence/pattern causes a corresponding sequence/pattern of detectable load changes at the charger coil 248. This sequence of load changes, which is referred to herein as implant detuning of the inductive power link 240 or an implant detuning sequence, is detectable via current changes at the charger coil 248.

In accordance with the embodiments presented herein, the implant controller 226 is configured to alter the resonant tank circuit 250 so as to vary the impedance of the resonant tank circuit 250 in accordance with a predetermined pattern. As noted, each variation in the impedance can be detected as a corresponding current change at the charger coil 248. As described further below, by monitoring the current through the charger coil 248 (e.g., via sensor 241), the charger controller 242 of the charger coil 248 can interpret these changes as a binary signaling code (i.e., a series of binary bits with values of either "0" or "1"). Therefore, at 372 of FIG. 3A, the implant controller 226 varies the impedance of the resonant tank circuit 250 in a manner that results in a series of first and second currents (i.e., "0" or "1" bit values) at the charger coil 248. When a predetermined current pattern (i.e., signaling code) is detected at the external charger 203, the external charger 203 terminates/disables the transmission of power to the cochlear implant 200.

The implant controller 226 may use a number of different techniques to vary the impedance of the resonant tank circuit 250 and, accordingly, to detune the implant resonant tank of the inductive power link 240 to signal to the external charger 203 that power transmission should be disabled. For example, in the specific embodiment of FIG. 3A, the implant controller 226 is configured to alternate the tuning of the resonant tank circuit 250 between 6.78 MHz and 5 MHz a predetermined number of times (e.g., a pattern comprising three (3) alternations between 6.78 MHz and 5 MHz) within a predetermined or selected time period, which results in a corresponding sequence of current changes at the charger coil 248. The implant controller 226 alternates the tuning of the resonant tank circuit 250 between 6.78 MHz and 5 MHz by selectively adding or removing inductance or capacitance to the resonant tank circuit 250. As described further below, the resonant tank circuit 250 may include elements e.g., switches that can be opened/closed to add or remove inductance or capacitance in the resonant tank circuit 250.

As described further below, alternating the tuning of the resonant tank circuit 250 between 6.78 MHz and 5 MHz is one example technique for load modulating the inductive power link 240. In another example, the implant controller 226 is configured to repeatedly electrically short and open the resonant tank circuit 250 a predetermined number of times within a predetermined/selected time period. Similar to the above embodiment, repeatedly electrically shorting and opening the resonant tank circuit 250 drastically varies the impedance of the resonant tank circuit 250. Each variation in the impedance can be detected as a corresponding current change at the charger coil 248 which, as noted above, is detected by the implant impedance sensor 241 and can be interpreted by the controller 242 as a binary signaling code that, when a predetermined signaling code is received, causes the external charger 203 to terminate/disable the transmission of power to the cochlear implant 200. Techniques for detuning and/or shorting the resonant tank circuit 250 are described further below with reference to FIGS. 4A and 4B.

Returning to the example of FIG. 3A, after signaling to the external charger to terminate/disable the transmission of power to the cochlear implant 200, the rechargeable battery 230 is disconnected from the resonant tank circuit 250. The method then returns to 361 and then to 370 (via the determinations at 361 and 362). At 370, the implant controller 226 determines that the rechargeable battery 230 is now disconnected from the resonant tank circuit 250 and, as such, the method proceeds to 376. At 376, a determination is made as to whether or not the resonant tank circuit 250 is tuned to 5 MHz. If the resonant tank circuit 250 is tuned to 5 MHz, then the method 360 returns to 361. If the resonant tank circuit 250 is not tuned to 5 MHz, then the resonant tank circuit 250 is adjusted so as to be tuned to 5 MHz at 378 and then the method 360 returns to 361.

In general, the operations of 361, 362, 370, and 376 are repeated until it is determined that the charger coil 248 is no longer coupled to the implantable coil 232 (at 361) or it is determined that the battery 230 should again be charged (at 362).

In summary, FIG. 3A illustrates an embodiment in which the cochlear implant 200 uses a predetermined implant detuning sequence (e.g., caused by intermittent detuning and retuning of the resonant tank circuit 250) to signal to the external charger 203 that the transmission of power to the cochlear implant should be terminated. That is, the predetermined sequence of intermittent detuning or shortening is initiated by the implant controller such that the external charger device may detect this particular sequence and ceases to operate. The predetermined sequence is limited in time (e.g., a few seconds), but the resonant tank circuit 250 may remain detuned or shortened at the end of this sequence, regardless of whether or not the sequence is detected by the external charger.

As noted, FIG. 3B is a flowchart illustrating corresponding operations of the external charger 203 based on (in response to) the operations of the cochlear implant 200 in FIG. 3A. Shown alongside FIG. 3B is FIG. 3C, which schematically illustrates the mode/status of the external charger 203 at the time the operations of FIG. 3B are performed.

Figure 3C:
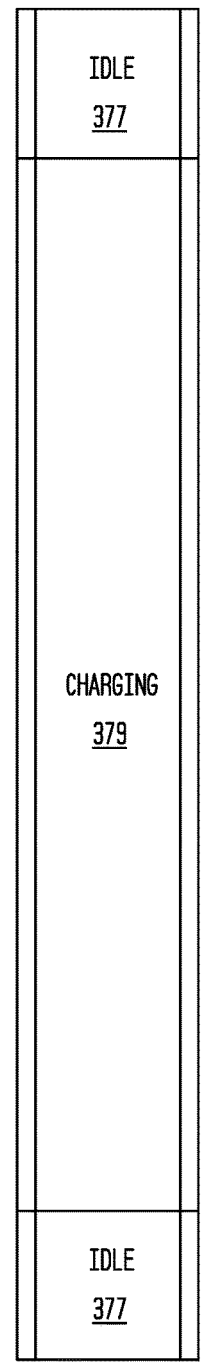
FIG. 3C is a schematic diagram illustrating a mode/status of the external charger of FIG. 3B at the time the operations of FIG. 3B are performed, in accordance with embodiments presented herein.

Referring first to FIG. 3C, shown are two modes for the external charger 203, referred to as an idle mode 377 and a charging mode 379. As shown, the external charger 203 may initially operate in the idle mode 377 in which no power is sent to the cochlear implant 200. Subsequently, the external charger 203 switches to the charging mode 379 in which power is sent to the cochlear implant 200 via the inductive power link 240. As described further below, in response to signaling received from the cochlear implant 200, the external charger 203 subsequently returns to the idle mode 377.

Referring next to FIG. 3B, shown is a method 380 that begins at 382 where the charging mode 379 is activated. That is, the external charger 203 is positioned (e.g., on the recipient's head) so that the charger coil 248 is coupled to the implantable coil 232. Additionally, the recipient or other user activates the transmission of power to the cochlear implant 200 (e.g., via a voice command, a user interface, such as a push button, etc.).

Once the charging mode 379 is activated, the external charger 203 continuously sends power to the cochlear implant 200 using an RF carrier (e.g., at 6.78 MHz). The external charger 203 also initiates a decode monitoring process 383 that includes the operations of 384, 386, 388, and 390. In the decode monitoring process 383, the external charger 203 (e.g., the charger controller 242) monitors the inductive power link 240 for a predetermined pattern of current changes that represent a predetermined binary signaling code that, when received, causes the external charger 203 to terminate the charging mode 379.

More specifically, at 384 the charger controller 242 senses/monitors the level (amplitude) of the current flowing within the charger coil 248 via the sensor 241. At 386, a determination is made as to whether or not the sensed current amplitude exceeds a predetermined threshold. The predetermined threshold is set at a current level where: (1) current levels above the threshold are associated with a first impedance and, as such, a first arrangement of the resonant tank circuit 250, and (2) current levels below the threshold are associated with a second impedance and, as such, a second arrangement of the resonant tank circuit 250.

In response to the determination at 386, a binary bit is written into the first-in-last-out (FILO) register 247 in the external charger 203. However, the value of the binary bit that is written into the register 247 depends on the results of the determination at 386. In particular, in the example of FIG. 3B, a determination at 386 that the sensed current in the charger coil 248 is above the threshold results in the writing of a value of "1" into the register 247, while a determination at 386 that the sensed current in the charger coil 248 is below the threshold results in the writing of a value of "0" into the register 247.

At 390, the register 247 is evaluated to determine whether a predefined sequence of binary bits is present in the register. In one example, the predefined sequence is "010101," which corresponds to three (3) sequential impedance alternations (e.g., a pattern of three sequential alternations of the tuning frequency from 6.78 MHz to 5 MHz).

If it is determined at 390 that the predefined sequence is not present in the register 247, then the method 380 returns to 384 and the operations of 384, 386, 388, and 390 are repeated until the predefined sequence is present in the register 247. Once the predefined sequence is present in the register 247, method 380 proceeds to 390 were the charging is terminated (i.e., the transmission of power to the cochlear implant 200 ceases). Once the charging is terminated, the external charger 203 returns to the idle mode 377.

In certain examples, the external charger 203 is configured to further determine whether the predefined sequence has been written into the register 247 within a predetermined limited time period. In such examples, the method 380 only proceeds to 390 if the predefined sequence was written to the register 247 within the time period. Such embodiments ensure that the charging is terminated in response to intended adjustments in the resonant tank 250, as described above, rather than to random noise or other unintended variations that could cause the entry of different binary bits into register 247.

FIG. 3B also illustrates a final optional step at 394 where the recipient, caregiver, or other user can be notified that the charging has ceased and/or that rechargeable battery 230 is fully charged. This notification may be beneficial in that it enables the recipient or user to proactively decouple the external charger 203 from the cochlear implant 200 (i.e., remove the external charger from the recipient's head).

In the above examples, the cochlear implant 200 uses the inductive power link 240 to signal to the external charger 203 that charging of the rechargeable battery 230 is to be terminated. This signaling is performed by altering the arrangement of the resonant tank circuit 250 so as to detune the resonant tank circuit (i.e., change the impedance of the resonant tank circuit 250 so as to cause a detectable change in the current flow at the charger coil 248). After performing the signaling to the external charger 203, the cochlear implant 200 is configured to disconnect the rechargeable battery 230 from the resonant tank circuit 250 and to detune the resonant tank circuit 250 to a non-optimal charging frequency, such as 5 MHz.

Although examples of detuning sequences have been described above, one of ordinary skill in the art would appreciate that any of a variety of methodologies can be implemented to signal to an external charger to cease providing power to the implanted device. As such, embodiments of the present invention are not limited to the implementation of the specifically described detuning sequences. In addition, although one methodology for a charging algorithm has been illustrated and described, one of ordinary skill in the art would appreciate that any of a variety of charging algorithms that prevent implant overheating can be implemented in accordance with embodiments of the present invention. Therefore, embodiments of the present invention are not limited to the methodology described with reference to FIGS. 3A-3C.

Figure 4A:
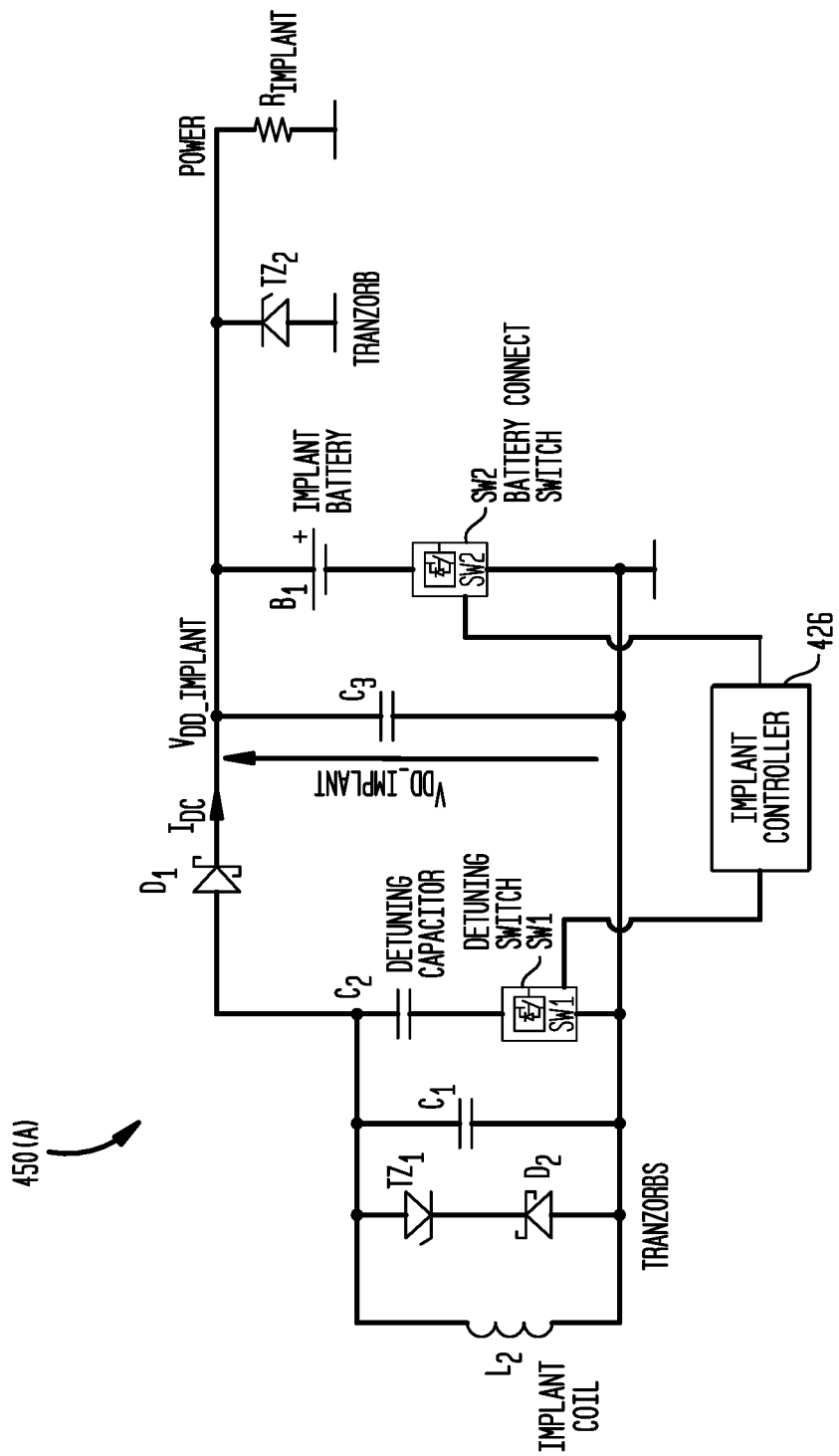
FIG. 4A is a schematic diagram illustrating a resonant tank circuit, in accordance with embodiments presented herein.
Figure 4B:
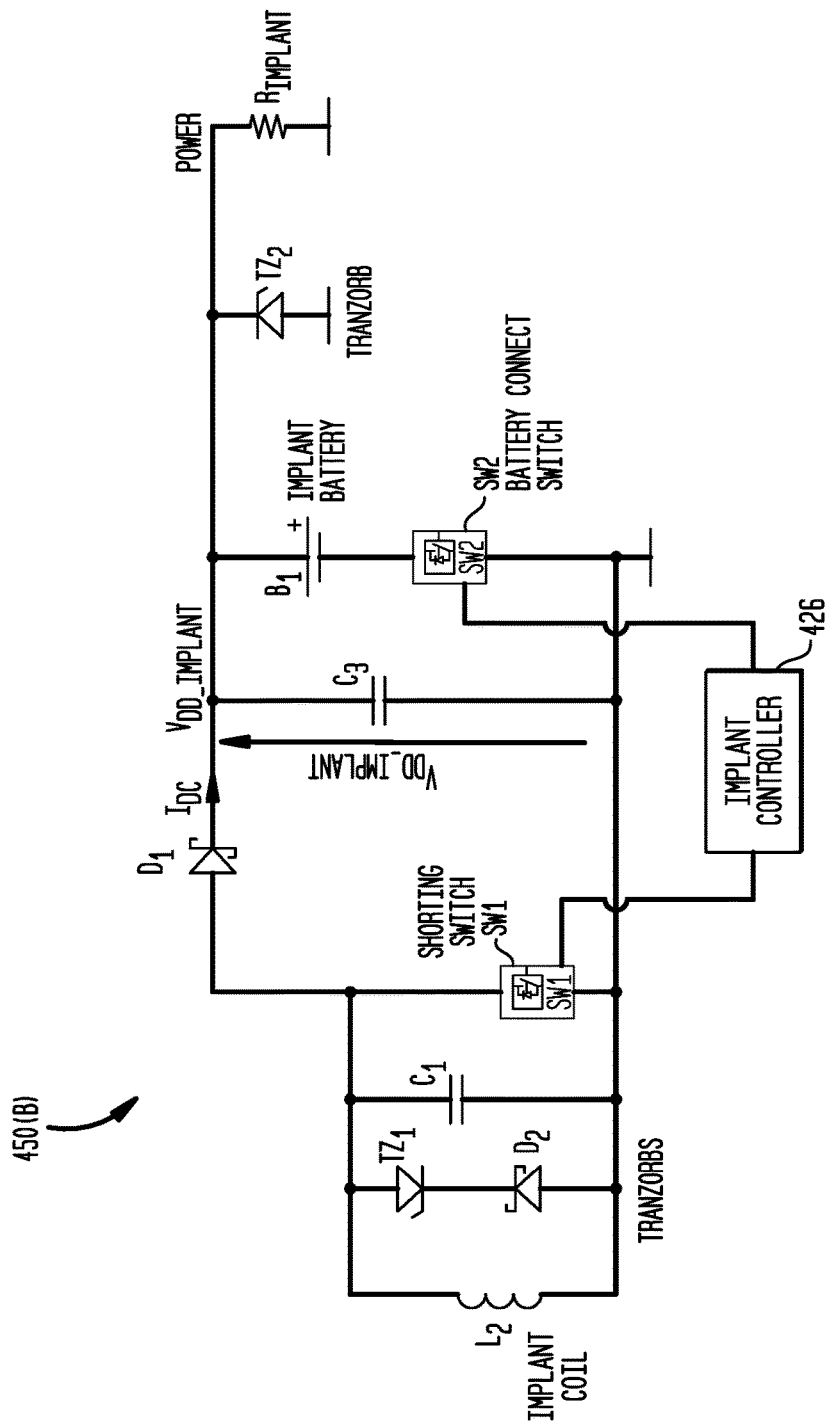
FIG. 4B is a schematic diagram illustrating another resonant tank circuit, in accordance with embodiments presented herein.

It is also to be appreciated that resonant tank circuits in accordance with embodiments presented herein may have a number of different circuit arrangements and may include a number of different circuit elements. FIGS. 4A and 4B illustrate two example arrangements for resonant tank circuits in accordance with embodiments presented herein.

More specifically, FIG. 4A illustrates an example resonant tank circuit 450(A) that includes, among other elements, an implantable coil represented by $L_2$ and a first capacitor $C_1$. Also shown in FIG. 4A is a second capacitor $C_2$, sometimes referred to herein as a detuning capacitor, and a detuning switch SW1. The detuning switch SW1 is operable, under the control of an implant controller (e.g., implant controller 226), to selectively connect capacitor $C_2$ in parallel with capacitor $C_1$ a predetermined number of times within a predetermined/selected time period Selectively connecting capacitor $C_2$ in parallel with capacitor $C_1$ by closing detuning switch SW1 detunes the resonant tank circuit 450(A). As such, detuning the resonant tank circuit 450(A) a predetermined number of times within a predetermined/selected time period signals to a closely coupled external charger that charging should be terminated.

FIG. 4A illustrates an arrangement in which the tuning of the resonant tank circuit 450(A) may be changed, for example, between 6.78 MHz and 5 MHz. FIG. 4B illustrates an alternative arrangement in which an example resonant tank circuit 450(B) includes, among other elements, an implantable coil represented by $L_2$ and a capacitor $C_1$. Also shown in FIG. 4B is a shorting switch SW2. The shorting switch SW2 is operable, under the control of an implant controller (e.g., implant controller 226), to selectively electrically short and open the resonant tank circuit 450(B) a predetermined number of times within a predetermined/selected time period. Selectively closing the shorting switch SW2 shorts the resonant tank circuit 450(B) to ground. As such, shorting and opening the resonant tank circuit 450(B) a predetermined number of times within a predetermined/selected time period signals to a closely coupled external charger that charging should be terminated.

Figure 4C:
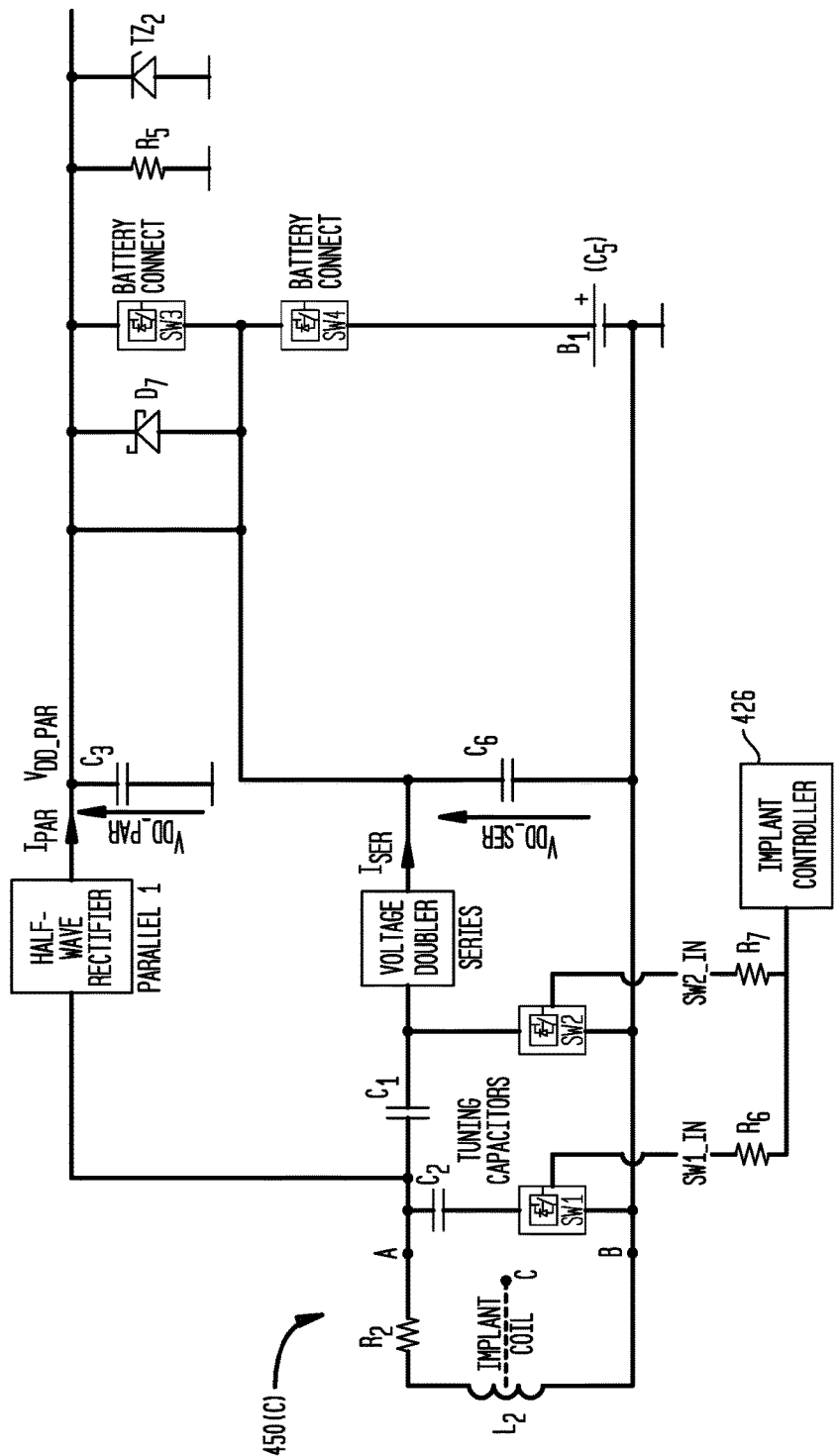
FIG. 4C is a schematic diagram illustrating another resonant tank circuit, in accordance with embodiments presented herein.

Various example arrangements for resonant tank circuits in accordance with embodiments presented herein are not only limited to parallel resonant tank circuits shown in FIGS. 4A-4B, but may also apply to series resonant tanks or combinations thereof. For example, FIG. 4C illustrates an alternative arrangement for a resonant tank circuit 450(C) configured to provide series and parallel resonance arrangements. In the example of FIG. 4C, during series resonance the switches SW1 and SW2 are open and during parallel resonance both switches SW1 and SW2 are electrically closed. In FIGS. 4A-4C, switches SW1 and SW2 may both be controlled by an implant controller (e.g., implant controller 226) which has been omitted from FIG. 4C for ease of illustration.

FIG. 5 is a high-level flowchart of a method 519 in accordance with embodiments presented herein. Method 519 begins at 521 where a resonant tank circuit of an implantable medical device receives power from an external charging device via an inductive link. At 523, the received power is used to charge a rechargeable battery that is electrically connected to the resonant tank circuit. At 525, a determination is made that the rechargeable battery has reached an end-of-charge condition. At 527, the inductive link is used to send a predetermined signaling code to the external charger to disable transmission of power by external charging device.

As noted above, presented herein are techniques in which an implantable component can use an inductive power link to signal to an external charging device that the charging of an implantable rechargeable battery should be terminated. In particular, the implantable component uses a predetermined implant detuning pattern/sequence (e.g., caused by intermittent detuning and retuning of an implant resonant tank circuit) to send a predetermined binary signaling code to the external charging device. Upon detection of the binary signaling code, the external charging device is configured to terminate the transmission of power to the implantable component. In addition, after signaling to the external charging device that transmission of power should be terminated, the implantable component can also electrically disconnect the rechargeable battery from the resonant tank circuit and detune the resonant tank circuit.

The techniques presented herein may result in a reduction in the heat implanted in implantable components and provide better compliance with regulatory requirements that make use of industrial, scientific and medical (ISM) radio bands for charging operations, while still providing dual frequency operation so as to remain backwards compatible. The techniques presented herein may also make use of standard charging protocols and may be used with a number of different charging devices. Additionally, a direct data link from the implantable component to the external component is not required.

Although embodiments have been primarily described with reference to auditory prostheses, it is to be appreciated that the techniques presented herein may be implanted in other implantable medical device.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable medical device, comprising:
a resonant tank circuit including an implantable coil coupled to an external coil of an external charging device via an inductive link so as to receive power from the external charging device via the inductive link;
a rechargeable battery electrically connected to the resonant tank circuit so as to be charged using the power received from the external charging device; and
a controller configured to:
determine when charging of the rechargeable battery should be terminated, and
detune and retune the resonant tank circuit using a predetermined sequential pattern to signal to the external charging device that charging of the rechargeable battery should be terminated.

2. The implantable medical device of claim 1, wherein after detuning and retuning the resonant tank circuit in accordance with the predetermined sequential pattern, the controller is configured to electrically disconnect the rechargeable battery from the resonant tank circuit.

3. The implantable medical device of claim 2, wherein to repeatedly adjust one or more characteristics of the resonant tank circuit, the controller is configured to repeatedly detune the resonant tank circuit between first and second resonant frequencies a predetermined number of times.

4. The implantable medical device of claim 2, wherein to repeatedly adjust one or more characteristics of the resonant tank circuit, the controller is configured to repeatedly switch the capacitance of the resonant tank circuit from a first capacitance to a second capacitance a predetermined number of times.

5. The implantable medical device of claim 1, wherein to detune and retune the resonant tank circuit in accordance with the predetermined sequential pattern, the controller is configured to repeatedly adjust one or more characteristics of the resonant tank circuit a predetermined number of times.

6. The implantable medical device of claim 1, wherein to detune and retune the resonant tank circuit in accordance with a predetermined sequential pattern, the controller is configured to switch the impedance of the resonant tank circuit from a first impedance to a second impedance a predetermined number of times.

7. The implantable medical device of claim 1, wherein the resonant tank circuit has a first resonant frequency to receive power from the external charger, and wherein, after detuning and retuning the resonant tank circuit the controller is configured to detune the resonant tank circuit to a second resonant frequency that is different from the first resonant frequency.

8. The implantable medical device of claim 6, wherein the first resonant frequency resides in an industrial, scientific and medical (ISM) radio band.

9. The implantable medical device of claim 1, wherein the implantable medical device is a cochlear implant.

10. A method, comprising:
at a resonant tank circuit of an implantable medical device tuned to a first resonant frequency, receiving power from an external charging device via an inductive power link;
using the received power to charge a rechargeable battery that is electrically connected to the resonant tank circuit;
determining that the rechargeable battery has reached an end-of-charge condition;
repeatedly adjusting one or more characteristics of the resonant tank circuit a predetermined number of times to send a predetermined signaling code to the external charger to disable transmission of power by the external charging device; and
after sending the predetermined signaling code, detuning the resonant tank circuit to a second frequency.

11. The method of claim 10, wherein repeatedly adjusting one or more characteristics of the resonant tank circuit a predetermined number of times, comprises:
repeatedly changing an arrangement of the resonant tank circuit between a first arrangement and a second arrangement, using a predetermined sequence.

12. The method of claim 10, wherein repeatedly adjusting one or more characteristics of the resonant tank circuit a predetermined number of times, comprises:
repeatedly switching the resonant tank circuit between the first and second resonant frequencies a predetermined number of times to adjust an amount of current flowing through an external coil of the external charging device in accordance with a predetermined pattern, wherein the pattern indicates to the charging device that the rechargeable battery has reached the end-of-charge condition.

13. The method of claim 10, wherein repeatedly adjusting one or more characteristics of the resonant tank circuit a predetermined number of times, comprises:
alternatively electrical shorting and opening the resonant tank circuit a predetermined number of times.

14. The method of claim 10, further comprising:
after sending the predetermined signaling code, disconnecting the rechargeable battery from the resonant tank when it is determined that the rechargeable battery has reached an end-of-charge condition.

15. The method of claim 10, wherein repeatedly adjusting one or more characteristics of the resonant tank circuit a predetermined number of times load modulates the inductive link to adjust an amount of current flowing through an external coil of the external charging device in accordance with a predetermined pattern, wherein the pattern indicates to the charging device that the rechargeable battery has reached the end-of-charge condition.

16. A method, comprising:
transferring power signals from an external coil of a charging device to an implantable coil of an implantable medical device, wherein the external coil and implantable coil are coupled via an inductive link;
monitoring the inductive link for a predetermined implant detuning sequence comprising a series of detectable load changes having a predetermined sequential pattern;
detecting, at the external coil, the predetermined implant detuning sequence; and
upon detection of the predetermined implant detuning sequence, reducing the transfer of the power signals from the external coil to the implantable coil to substantially zero.

17. The method of claim 16, wherein monitoring the inductive coupling for a predetermined implant detuning sequence, comprising:
monitoring an amplitude of current flowing through the external coil.

18. The method of claim 17, wherein monitoring an amount of current flowing through the implantable coil comprises:
measuring the amplitude of the current flowing through the external coil at different times to produce a plurality of current amplitude values;
comparing each of the current amplitude values to a predetermined threshold level;
after each comparison of a current amplitude value to the predetermined threshold level, writing a binary value to a storage memory device, wherein each binary value is based on the results of the preceding comparison and is written to the storage memory device in sequence; and
validating binary values in the storage memory device for the presence of a predetermined binary code stored in the storage device.

19. The method of claim 17, wherein monitoring the inductive coupling for a predetermined implant detuning sequence, comprising:
  monitoring the amplitude of current flowing through the external coil with an implant impedance sensor.

20. The method of claim 16, wherein monitoring the inductive coupling for a predetermined implant detuning sequence, comprising:
  monitoring an amplitude of a voltage at the external coil.

21. The method of claim 16, wherein monitoring the inductive coupling for a predetermined implant detuning sequence, comprising:
  measuring one or more of back scattering or reflected load changes from the implantable medical device.

22. An implantable medical device, comprising:
  a resonant tank circuit including an implantable coil coupled to an external coil of an external charging device via an inductive link so as to receive power from the external charging device via the inductive link;
  a rechargeable battery electrically connected to the resonant tank circuit so as to be charged using the power received from the external charging device over a first frequency; and
  a controller configured to:
    determine when charging of the rechargeable battery should be terminated,
    sequentially change an arrangement of the resonant tank circuit between a first arrangement and a second arrangement, using a predetermined sequence so as to cause a corresponding sequence of detectable load changes at the external charging device; and
    detune the resonant tank circuit to a second frequency.

23. The implantable medical device of claim 22, wherein the controller is configured to:
  electrically disconnect the rechargeable battery from the resonant tank circuit.

24. The implantable medical device of claim 22, wherein sequentially changing the arrangement of the resonant tank circuit between a first arrangement and a second arrangement in accordance with a predetermined sequence repeatedly detunes and retunes the resonant tank circuit between first and second resonant frequencies a predetermined number of times.

* * * * *